United States Patent [19]
Burghard et al.

[11] Patent Number: 5,637,881
[45] Date of Patent: *Jun. 10, 1997

[54] METHOD TO DETECT NON-SPHERICAL PARTICLES USING ORTHOGONALLY POLARIZED LIGHT

[75] Inventors: Raymond Burghard, Bow, N.H.; Derek Aqui, San Jose; Peter Borden, San Mateo, both of Calif.

[73] Assignee: High Yield Technology, Inc., Sunnyvale, Calif.

[*] Notice: The term of this patent shall not extend beyond the expiration date of Pat. No. 5,347,138.

[21] Appl. No.: 421,572

[22] Filed: Apr. 11, 1995

Related U.S. Application Data

[63] Continuation-in-part of Ser. No. 41,088, Apr. 1, 1993, Pat. No. 5,347,138, and Ser. No. 414,145, Mar. 29, 1995, which is a continuation of Ser. No. 41,070, Apr. 1, 1993, abandoned.

[51] Int. Cl.[6] .................................................. G01N 15/06
[52] U.S. Cl. .................. 250/573; 356/343; 250/222.2
[58] Field of Search .................................... 250/573, 575, 250/574, 222.2, 225; 356/335, 336, 375, 343, 338, 37, 337

[56] References Cited

U.S. PATENT DOCUMENTS

| | | | |
|---|---|---|---|
| 4,701,051 | 10/1987 | Buchhave et al. | 356/336 |
| 5,037,202 | 8/1991 | Batchelder et al. | 356/336 |
| 5,133,602 | 7/1992 | Batchelder et al. | 356/375 |
| 5,266,798 | 11/1993 | Borden et al. | 250/573 |
| 5,296,910 | 3/1994 | Cole | 356/336 |
| 5,347,138 | 9/1994 | Aqui et al. | 250/573 |

*Primary Examiner*—Stephone Allen
*Attorney, Agent, or Firm*—Skjerven, Morrill, MacPherson, Franklin & Friel; Edward C. Kwok

[57] ABSTRACT

A structure and a method provide a quasi bright field particle sensor for the detection of non-spherical particles, using a laser beam of predetermined polarization. A phase shift caused by non-spherical particles passing through the laser beam is utilized to detect the presence of such particles. In one embodiment, a single laser beam is used to detect the concentration of non-spherical particles in the pump line receiving the exhaust gas from a process chamber.

10 Claims, 5 Drawing Sheets

POLARIZATION
WITHOUT SCATTER

POLARIZATION
WITH SCATTER

_5,637,881_

METHOD TO DETECT NON-SPHERICAL PARTICLES USING ORTHOGONALLY POLARIZED LIGHT

CROSS-REFERENCE

The present application is a continuation-in-part application of the patent application Ser. No. 08/414,145, entitled "A Quasi Bright Field Particle Sensor", by Peter G. Borden and Derek G. Aqui, assigned to High Yield Technology, filed on Mar. 29, 1995, now U.S. Pat. No. 5,606,418, which is a continuation application of patent application Ser. No. 08/041,070, entitled "A Quasi Bright Field Particle Sensor", by Peter Borden and Derek Aqui, assigned to High Yield Technology, filed on Apr. 1, 1993, now abandoned. The present application is also a continuation-in-part application of patent application, Ser. No. 08/041,088, now U.S. Pat. No. 5,347,138, filed Apr. 1, 1993 and issued Sep. 13, 1994, entitled "In Situ Real Time Particle Monitor For A Sputter Coater Chamber", by Derek G. Aqui and Peter G. Borden, and assigned to High Yield Technology.

BACKGROUND OF THE INVENTION

1. Field of the Invention

This invention relates to the use of polarized light to detect small particles. More specifically, this invention relates to a means for detection of non-spherical particles in a process chamber used for the manufacture of integrated circuits.

2. Discussion of the Related Art

Particle detection is widely used in vacuum process equipment, such as that involved in the processing of semiconductor wafers, because even a small number of particles in the manufacturing process can lead to substantial yield loss.

Most particle detectors or monitors are designed based on a dark field technique. Several examples of particle monitors using a dark field technique are disclosed in U.S. Pat. No. 4,739,177 to Peter Borden, entitled "Particle Detector for Wafer Processing Equipment," filed on Sep. 16, 1986 and issued on Jun. 19, 1988. In the dark field technique, a laser beam is projected through a region where particles are expected to pass, and photodetectors or photocells are placed off-axis near the laser beam to detect the light the particles scatter from the laser beam. In a dark field particle detector, the laser beam is not incident on the photodetector. (Hence, the term "dark field" technique.) The scattered light detected by the off-axis photodetector is converted to an electrical pulse that indicates the presence of the particle.

However, a dark field particle detector has numerous inherent limitations. In particular, such a particle detector is very sensitive to background light or noise. For example, when used as a particle detector in a sputtering process which uses plasma, light from plasma glows, or from dirt present on the optics, can scatter light from the laser beam to the photodetectors. Also, since the photodetectors of a dark field particle detector must be placed in close proximity to the laser beam, such a particle detector is inherently limited in where it can be deployed. In particular, such a dark field particle detector cannot be readily placed inside a processing chamber where the semiconductor wafers are being processed.

A bright field particle detector overcomes some of the difficulties encountered in the use of a dark field particle detector. In a "bright field" sensor or detector, a laser beam is shone directly on the sensing photodetector. Particles passing through the laser beam scatter light from the laser beam, thereby reducing its intensity and, consequently, reducing the photocell current when the laser beam impinges the photocell. Since a bright field particle detector does not require the photocells to be placed in close proximity to the laser beam along its path, the bright field technique allows the laser beam to be shone across processing chambers. Further, the bright field technique is inherently less sensitive to background light or noise, since the bright field detector receives only the input stimulus from a small angular aperture, which corresponds to the size of the laser beam.

Bright field sensors, however, are susceptible to shot noise. Thus, bright field sensors are traditionally regarded as lacking the requisite sensitivity for such applications as semiconductor wafer processing. Shot noise is the statistical noise generated in a photocell by the photon current, and is thus proportional to the square root of the laser power. The shot noise current in a photocell is given by the equation $$I_{shot} = \sqrt{2qPA(BW)} \qquad (1)$$

where q is the charge of an electron, P is the power of the laser, A is the conversion efficiency of the photocell (in amperes per watt), and BW is the bandwidth of detection.

Because shot noise is typically much higher in power than amplifier noise, shot noise limits the sensitivity of the best bright field sensors to detection of particles. In the state of the art, bright field sensors have a sensitivity of about 1 μm.

The dark and bright field sensors in the prior art do not distinguish between spherical and non-spherical particles. In many applications, the particles of interest are non-spherical. For example, most of the particles responsible for contamination in a processing chamber for integrated circuit manufacture are non-spherical (e.g. flakes from the chamber walls). However, the density of such non-spherical particles may be lower than that of spherical particles generated by homogenous nucleation in the plasma stream.

These spherical particles do not represent a source of contamination because either they form in the plasma gas stream downstream from the wafer being manufactured, or they form above the wafer but are suspended above the wafer by electric fields. Without a sensor that is insensitive to spherical particles, the high density of spherical particles produced by homogenous nucleation in the plasma gas stream may mask the relatively low density of non-spherical particles, thereby failing to detect particles which cause wafer contamination and lower manufacturing yield.

SUMMARY OF THE INVENTION

The present invention discloses a method for measuring the concentration of non-spherical particles in a process chamber. In one embodiment, a laser source emits a single beam of polarized light, consisting of two orthogonally polarized components of equal intensity, across the pump line receiving the flow of exhaust gas from the chamber. The rotation of the plane of polarization of the beam, resulting from the preferential scattering of one or the other of the polarized components by non-spherical particles passing in the pump line between the laser source and the detector, is measured by a detector.

The present invention is better understood after considering the detailed description below, in conjunction with the accompanying drawings.

DETAILED DESCRIPTION OF THE PREFERRED EMBODIMENTS

Figure 1:
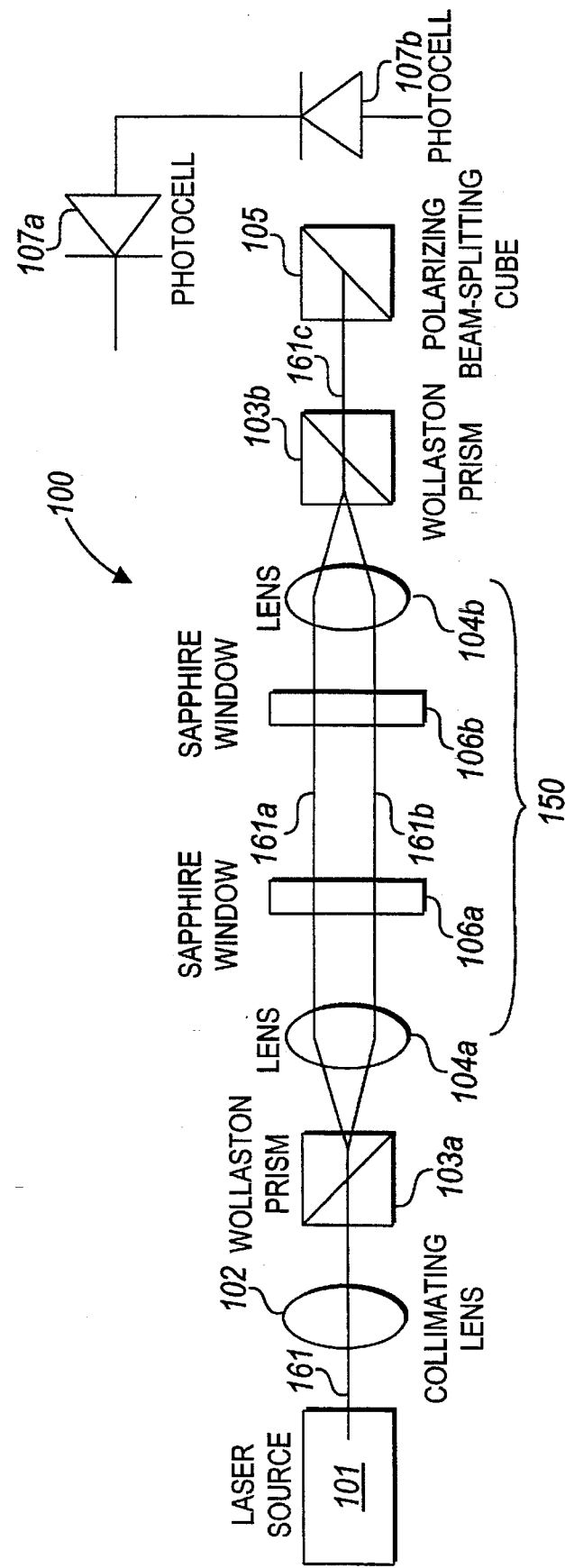
FIG. 1 shows a particle detector 100 in which a laser beam 161 is projected through a space 150 in which particles to be detected are present; laser beam 161 is detected by two photo cells 107a and 107b placed to receive orthogonal polarizations of light, in accordance with the present invention.

FIG. 1 shows an embodiment of the present invention in which particle detector 100 projects a laser beam 161 through space 150 in which the particles to be detected are. As shown in FIG. 1, laser source 101 projects a polarized laser beam 161 through collimating lens 102 to form a laser beam of parallel rays. Typically, laser source 101 is a low noise laser diode, such as the Sony 301, available from Sony Corporation, Japan. Sony 301 operates at a power of 50 mW, and provides a laser beam of wavelength of about 800 nanometers. Laser diodes, such as the Sony 301, have typical polarization ratios in excess of 1000. A number of commercially available lenses are suitable to be used as collimating lens 102; for example, collimating lens 102 can be made from SPL lens available from Nippon Sheet Glass of Tokyo, Japan.

Laser beam 161 is polarized at 45° to the paper, so that the components of laser beam 161, i.e. the components of laser beam 161 in the plane of the paper and perpendicular to the plane of the paper, are of equal power. Polarized laser beam 161 then passes through Wollaston prism 103a, which splits laser beam 161 into laser beams 161a and 161b, which are orthogonally polarized with respect to each other. A suitable wallaston prism for Wollaston prism 103a is model WQ12-05 from Karl Lambrecht, Inc. of Chicago, Ill. This Wollaston prism provides a splitting of 0.5°, resulting in laser beams 161a and 161b being separated by about 1 mm at the 75 mm focal length of lens 104a.

Laser beams 161a and 161b emerge at an angle with respect to each other from Wollaston prism 103a. This angle between laser beams 161a and 161b is typically a few tenths of a degree. Laser beams 161a and 161b then pass through lens 104a, which converts laser beams 161a and 161b to essentially parallel beams without affecting their relative polarization.

After passing through space 150, laser beams 161a and 161b are then combined by lens 104b and Wollaston prism 103b. Lens 104b and Wollaston prism 103b are each substantially identical to lens 104a and Wollaston prism 103a to form a combined laser beam 161c of 45° polarization. Lens 104a and 104b are common cylindrical lenses with focal lengths chosen to provide the necessary length of substantially parallel beam through the area of particle detection. The combined laser beam 161c then passes through a polarizing beam splitting cube 105 oriented so that, when no particles are detected, the combined laser beam 161c impinges only on photocell 107b. A suitable polarizing beam splitting cube for use as polarizing beam splitting cube 106 is model TFPC 12 from Karl Lambrecht, Inc., which provides a selectivity between polarizations of better than 1000.

Figure 2A:
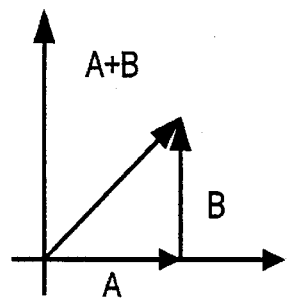
FIG. 2a shows that, when no particle is present in either laser beam 161a or 161b, the combined laser beam 161c has a polarization of 45°.

The operation of particle monitor 100 is next disclosed. When neither laser beam 161a nor laser beam 161b encounters a particle, laser beams 161a and 161b each have substantially equal intensity, so that the combined laser beam 161c has a polarization angle of 45°, as shown in FIG. 2a. FIG. 2a shows the polarization of laser beam 161c, as a vector sum of orthogonally polarized laser beams 161a and 161b, when no particle is present in either laser beam 161a or laser beam 161b.

Figure 2B:
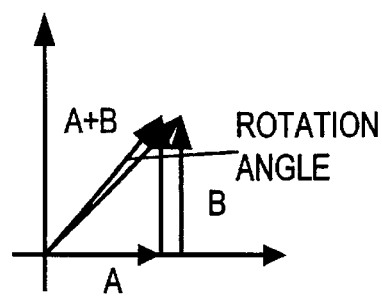
FIG. 2b shows the change in polarization in combined laser beam 161c as a result of a particle passing through one of laser beams 161a and 161b.

However, when a particle is encountered by laser beam 161a, the intensity of laser beam 161a is reduced. As a result, the combined laser beam 161c will have a polarization other than 45°, as shown in FIG. 2b. FIG. 2b shows the polarization of laser beam 161c, as a vector sum of laser beams 161a and 161b, when the intensity of laser beam 161a is reduced due to the presence of a particle in laser beam 161a. Consequently, the combined laser beam 161c entering polarizing beam splitting cube 105 is split, and the component split from combined laser beam 161c impinges onto photocell 107a to cause a photo current in photo cell 107a, thereby indicating the presence of a particle.

Since laser beam 161c impinges on photocell 107b, particle monitor 100 is substantially a bright field detector. Hence, the present invention allows detection of particles in "bright field" particle monitor 100. However, in particle monitor 100, photocell 107a receives incident light beam from the combined laser beam 161c, only when a particle passes through either laser beam 161a or 161b. Thus, no shot noise is generated in photocell 107a. Consequently, sensitivity of particle monitor 100, unlike other bright field sensors, does not suffer degraded performance due to shot noise.

Furthermore, photocell 107b which receives the total energy of combined laser beam 161c, when there is not a particle in either laser beam 161a or 161b, can be used as a noise reference to cancel laser noise. Thus, particle monitor 100, whose primary noise component is amplifier noise, achieves both the sensitivity of a dark field sensor, and the advantages of a bright field particle sensor.

Particle monitor 100 detects both radially symmetrical and asymmetrical particles. In some applications, detecting only asymmetrical particles, rather than both, is sufficient. In such applications, laser beam 161 need not be split into laser beams 161a and 161b. Indeed, in the applications of interest, i.e. particle detection in semiconductor manufacturing equipment, particles are seldom spherical. To understand why a single laser beam does not detect radially symmetrical particles, consider the case where laser beams 161A and 161B are brought closer and closer together, until they overlap. Now, if a spherical particle pass through the overlapped beams, the particle scatters equally both laser beam 161a and 161b, i.e. both polarization components. The resulting polarization in laser beams 161c does not rotate under this condition, and no signal is generated at photocell 107a. However, a non-spherical particle scatters preferentially one polarization more than the orthogonal polarization. For instance, a rod-shaped particle scatters light polarized along the axis of the rod less preferentially than light polarized off-axis. Thus, the resulting polarization of laser beam 161c scattered by a rod-shaped particle is rotated, and a single beam is sufficient to detect the presence of such a particle. A single-beam particle monitor can be achieved for detection of non-spherical particles by omitting the Wollaston prisms 103a and 103b.

Figure 5:
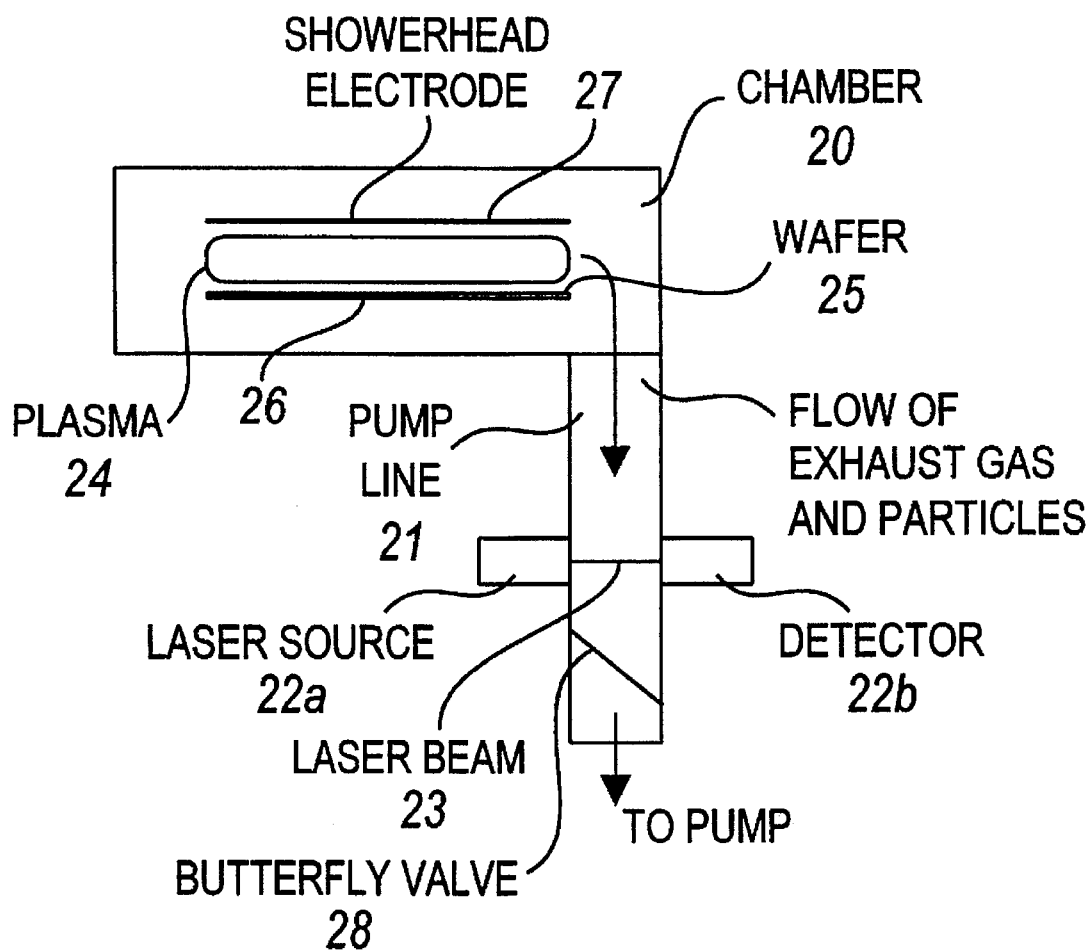
FIG. 5 shows a plasma process chamber with a particle sensor installed in the pump line.
Figure 6:
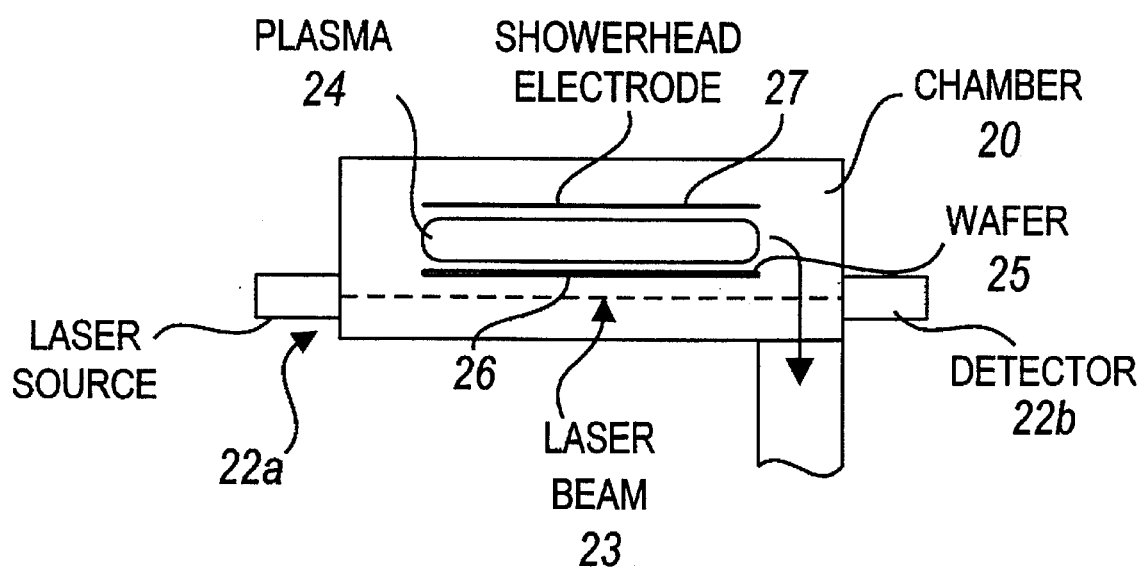
FIG. 6 shows a particle sensor attached directly to a plasma process chamber.

An example of an application where the detection of only non-spherical particles is desirable is shown in FIG. 5. As shown in FIG. 5, process chamber 20 used for the manufacture of integrated circuits, contains a plasma gas stream 24 above wafer 25. Wafer 25 rests on a horizontal electrode 26. Plasma 24 is contained between electrode 26 and a "shower head" electrode 27. During operation pump line 21 removes exhaust gas and particles from chamber 20 through butterfly valve 28. A quasi-bright field sensor 22, such as monitor 100 of FIG. 1, that detects only aspherical particles, is attached to pump line 21. Field sensor 22 contains laser source 22a, which passes a single polarized beam 23 across pump line 21, and a detector 22b that detects the rotation in the plane of polarization of beam 23 caused by non-spherical particles in pump line 21 passing between laser source 22a and detector 22b. (In another embodiment, illustrated by FIG. 6, laser source 22a and detector 22b are attached directly to chamber 20.)

Homogenous nucleation in plasma gas stream 24 often generates spherical particles. However, such particles do not land on the wafers because either they form in plasma gas stream 24 downstream from wafer 25, or they form above wafer 25 but are suspended above wafer 25 by electric fields. Without a sensor that is insensitive to spherical particles, the high density of such particles produced by homogenous nucleation in plasma gas stream 24 would tend to mask the relatively low density of non-spherical particles due to such causes as flaking from the chamber walls, which tend to create non-spherical particles. These aspherical particles can be deposited on wafer 25, thereby adversely impacting the yield of the manufacturing process.

In applications where corrosive gasses are present, sapphire windows 106a and 106b are placed on the chamber side of lenses 104a and 104b. Windows 106a and 106b are made from sapphire of (0001) crystal orientation, since this sapphire crystal orientation does not affect the polarization of the laser beam passing through them, and sapphire is not significantly attacked by corrosive species, such as fluorine and reactive fluorine by-products commonly found in a plasma etcher.

Performance of particle monitor 100 can be calculated by determining the amount of light a particle scatters from laser beam 161, when a single beam is used, or from one of its component beams 161a and 161b, when two laser beams are used. The light reaching the detection photocell 107a is a function of the amount of light scattered by the particle passing through laser beam 161 or the component laser beams 161a and 161b. The noise in the detection photocell 107a is determined by shot noise, resulting from background light reaching the detection photocell 107a. Such background light can be caused by imperfection in the laser polarization components, i.e. laser source 101 and Wollaston prisms 103a and 103b, and polarizing beam splitter cubes 105. With the signal and noise intensities known, the signal to noise ratio is determined.

For a typical system, laser beam 161 is focussed to a thickness $$t_0 = \frac{\lambda f}{\pi t_1} \quad (2)$$

where $t_1$ is the thickness at the lens, $\lambda$ is the wavelength, and f the focal length.

In a typical system with a focal length of 7.5 cm and a beam thickness of 1 mm at the lens, the beam thickness at laser beam 161's focus is approximately 0.004 cm. The typical beam width is 3 mm, which remains constant through the system.

The scattering cross-section for a particle is easily calculated using Mie scattering theory. A discussion of the Mie scattering theory is found in "Light Scattering by Small Particles" by H. C. van de Hulst, published by Dover books. The noise level is calculated using equation (1) given above, with the bandwidth given by the equation $$BW = \frac{0.3v}{t_0}, \quad (3)$$

where v is the particle velocity.

Equation (3) depends on the relation that the pulse width generated by a particle passing through the beam depends upon the particle velocity and the thickness to the beam. The factor of 0.3 arises because the pulse is Gaussian rather than sinusoidal in shape and represents a ½ cycle.

Figure 3:
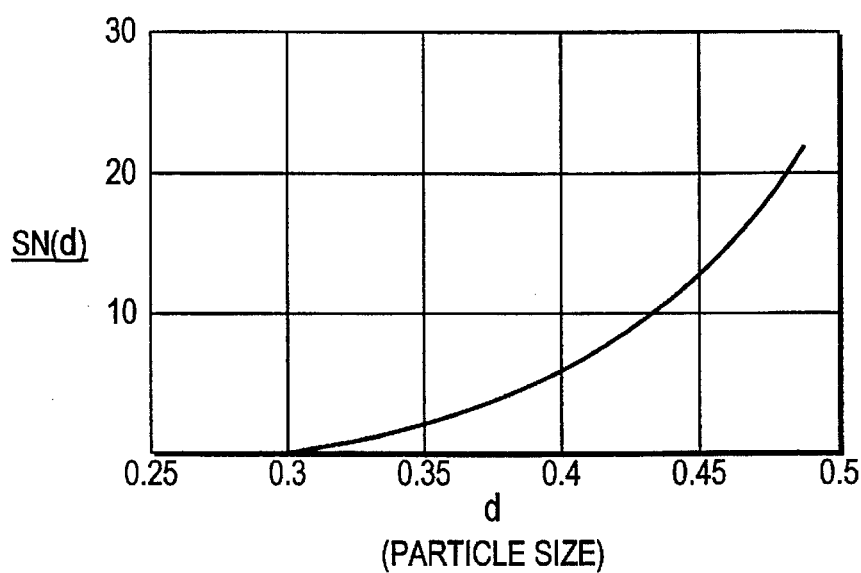
FIG. 3 is a graph plotting the signal-to-noise (s/n) ratio versus the particle size detectable by particle monitor 100.

Using these factors, and assuming that (a) the main beam is attenuated by a factor of 1000 in reference photocell 107b and (b) photocell 107a's responsivity is 0.5 amps/watt, the graph in FIG. 3 plots the signal-to-noise (s/n) ratio versus particle size in microns for particles with an index of refraction of 1.5. A s/n ratio greater than 2 is normally needed to detect a particle.

Figure 4:
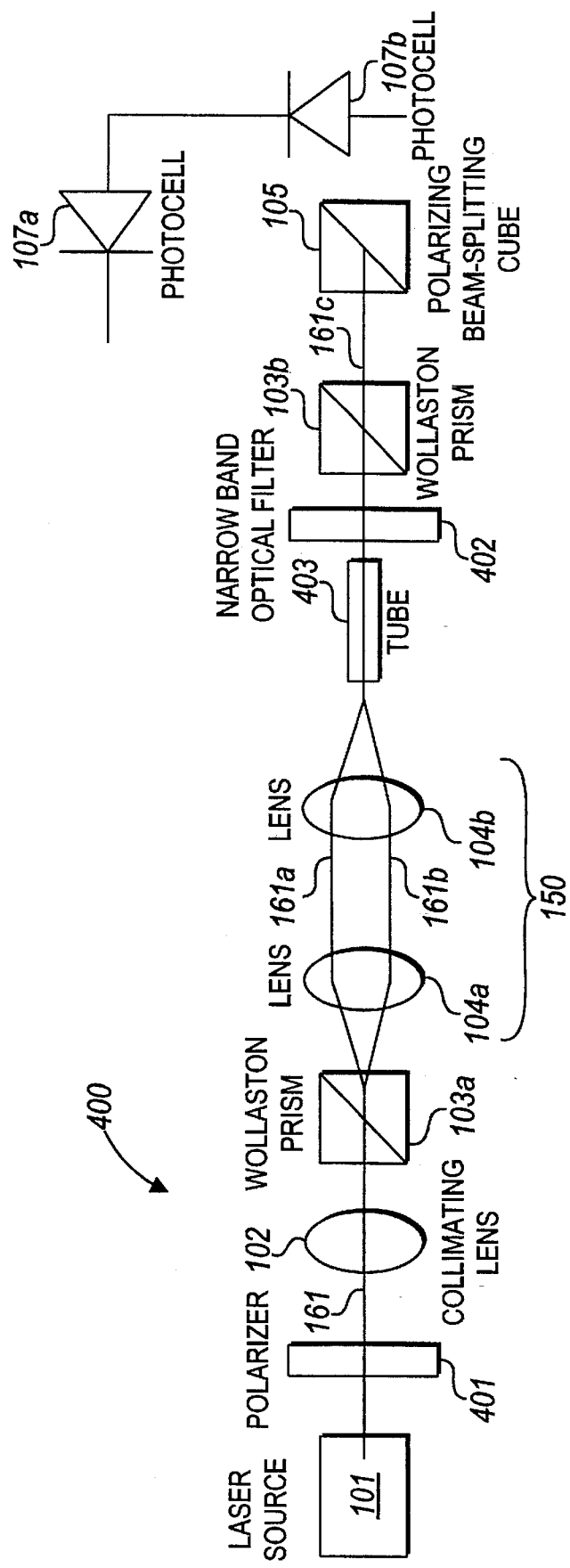
FIG. 4 shows a particle monitor 400 which is a variation in configuration of particle monitor 100 shown in FIG. 1.

In practice, performance of particle monitor 100 can be enhanced by the following variation in its configuration, such as illustrated by particle monitor 400 in FIG. 4:

(i) a polarizer 401 can be placed after laser source 101 to remove polarization noise. A good polarizer to be used is a beam splitting cube oriented so that any radiation from laser source 101 out of the primary polarization is directed 90° out of the system;

(ii) a narrow band optical filter 402 can be placed before the final detector photocell 107a to remove optical noise from the ambient;

(iii) laser beam 161 can run through a long, narrow tube 403 prior to reaching the receiver optics (e.g. Wollaston prism 103b) to limit the viewed aperture, thereby restricting the amount of background noise that enters particle monitor 100;

(v) the signal from reference photocell 107b can be used in a circuit to cancel the laser noise; and (vi) the signal of reference photocell 107b can be attenuated to maintain linearity when using high laser powers.

The above detailed description is provided to illustrate the specific embodiments of the present invention and should not be construed as limiting. Numerous variations and modifications are possible within the scope of the present invention. The present invention is defined by the following claims:

We claim:

1. A system comprising:
   a process chamber; and
   a particle monitor that uses a linearly-polarized laser beam to detect the concentration of non-spherical particles in said chamber.

2. A system as in claim 1, wherein said means comprises:
   a laser source that emits a single beam of polarized light; and
   a detector, located opposite said laser source, for measuring a rotation in polarization in said beam resulting from a non-spherical particle passing through said beam of polarized light.

3. A system as in claim 2, wherein said means further comprises a polarizer positioned for removing polarization noise in said laser beam.

4. A system as in claim 2, wherein said means further comprises a narrow band optical filter, placed before said detector, for removing noise from background light.

5. A system as in claim 2, wherein said means further comprises a tube through which said laser beam travels, said tube restricting the amount of background noise reaching said detector.

6. A system as in claim 2 that further comprises a pump line, coupled to said process chamber, for removing exhaust gas and particles from said chamber and wherein said laser source and said detector are mounted on said pump line.

7. A system as in claim 2, wherein said laser source and said detector are mounted on said process chamber.

8. A method for measuring the concentration of non-spherical particles in a process chamber comprising the steps of:

sending a single beam of linearly polarized light from a laser source to a detector opposite said laser source; and measuring the rotation in polarization in said beam of polarized light, when a non-spherical particle passes through the beam.

9. A method as in claim 8, further comprising the steps of mounting said laser source and said detector on a pump line, coupled to said process chamber, wherein said pump line removes exhaust gas and particles from said chamber and wherein said beam travels in a direction perpendicular to the direction of the flow of said exhaust through said pump line.

10. A method as in claim 8, wherein said laser beam travels across said process chamber.

* * * * *